United States Patent [19]

Nandagiri et al.

[11] 4,261,972
[45] Apr. 14, 1981

[54] HYDROALCOHOLIC AEROSOL HAIR SPRAYS

[75] Inventors: Arun Nandagiri, Dover; Uma Tripathi, Oakland, both of N.J.

[73] Assignee: American Cyanamid Company, Stamford, Conn.

[21] Appl. No.: 78,253

[22] Filed: Sep. 24, 1979

[51] Int. Cl.³ .......................... A61K 7/06; A61K 7/11
[52] U.S. Cl. .......................................... 424/47; 424/81
[58] Field of Search ........................................... 424/47

[56] References Cited

U.S. PATENT DOCUMENTS

| B 464,491 | 3/1976 | Pavlik et al. | 424/47 |
| 4,030,512 | 6/1977 | Papantoniou et al. | 424/47 |
| 4,134,968 | 1/1979 | Stebles | 424/47 |
| 4,165,367 | 8/1979 | Chakrabarti | 424/47 |
| 4,173,627 | 11/1979 | Madrange et al. | 424/47 |

FOREIGN PATENT DOCUMENTS

| 46-10434 | 3/1971 | Japan | 424/47 |
| 50-101540 | 8/1975 | Japan | 424/47 |

*Primary Examiner*—Dale R. Ore
*Attorney, Agent, or Firm*—Charles J. Fickey

[57] ABSTRACT

A pressurized hair spray composition having reduced flammability, a superior hair holding resin and containing 20 to 35 percent aliphatic hydrocarbon and 2 to 30 percent water.

5 Claims, No Drawings

HYDROALCOHOLIC AEROSOL HAIR SPRAYS

The present invention relates to a pressurized hair spray composition containing a superior hair holding resin in a formulation which has reduced flammability.

Various compositions containing hair spray resins suitable for holding hair in place are known. They include resins such as vinyl acetate—crotonic acid copolymer, polyvinyl pyrrolidone, vinyl pyrrolidone-vinyl acetate copolymers and copolymers of methyl vinyl ether and monoethyl or monobutyl esters of maleic acid. Compositions containing such resins are disclosed in various U.S. Patents. U.S. Pat. No. 3,922,341 is an example wherein an alcoholic solution of the resin is pressurized with trichlorofluromethane, diflurodichloro methane and nitrous oxide.

The propellants that were used in such hair spray formulations were normally fluorocarbons. These fluorocarbons were alleged to damage the ozone layer and their use in consumer products has been restricted. Hydrocarbon propellants such as propane, n-butane, isobutane and mixtures thereof are now widely used as propellants. Hydrocarbon propellants are highly flammable and it is necessary to include a flame retardant to suppress the flammability of such compositions. Typical formulations containing water as the flame retardant are described in copending, commonly assigned Nandagiri et al., U.S. patent application Ser. No. 844,241, filed Oct. 21, 1977 now U.S. Pat. No. 4,164,562. The formulations described in the above application contain 2 to 12 percent water to reduce the flammability of the said composition. The polymer used in the above hair spray composition is a copolymer of methyl vinyl ether and monoethyl or monobutyl ester of maleic acid in which at least 10 percent of the free carboxylic acid groups are neutralized with an organic base, such as ammonia, dimethyl-, di- and triethyl-, and triisopropanol amine, and 2-methyl-2-amino-1-propanol. Since the polymer is not water soluble, the amount of water used is critical. Below 2 percent there is very little notable effect on the flammability, above about 12 percent the polymer will precipitate from solution. Preferred results are obtained by the addition of about 8 percent water.

The present invention provides a composition wherein the incompatibility with higher concentrations of water is not encountered thus enabling the use of water at levels higher than 12 percent. This greatly enhances the flame retardant properties of the fomulations. The polymer used in such a composition is water soluble, and belongs in a broad class of acrylic and/or methacrylic resins. Examples of such resins are Amphomer made by National Starch Inc. (Octylacrylamide/Acrylates/Butylamino ethyl Methacrylate Polymer), Stepanhold made by Stepan (PVP/Ethyl Methacrylate/Methacrylic Acid) and copolymers of Methyl Methacrylate/Methacrylic acid. These acrylic resins generally form films which are brittle and do not perform well in hair holding formulas unless they are plasticized. The use of plasticizers in hair sprays causes other problems such as oily feel on hair and continued use of such formulations causes the hair to get dirty very quickly.

We have found that the addition of large quantities of water to an acrylic based resin formulation performs equally well in plasticizing the resin, without any of the associated problems described above. We have also found that the use of large quantities of water helps to restore the moisture content of hair which may be lost by the use of blow dryers and hot combs.

The copolymers of methyl vinyl ether and monobutyl of monoethyl esters of maleic acid described in the patent application referenced above, are moisture sensitive and their holding power is greatly impaired by the addition of water to the formula. The acrylic resins are not affected by such additions of water enabling them to be superior in performance when formulated in hydroalcoholic concentrates.

The following examples are given by way of illustration only and are not intended as limitations of this invention.

EXAMPLE 1

An aerosol hair spray is prepared by mixing the following ingredients:

| Ingredients | Percent W/W |
| --- | --- |
| Ethanol Anhydrous | q.s. |
| 2-Amino-2 methyl-1 propanol | 0.32 |
| Amphomer* | 2.00 |
| Water | 25.00 |
| Fragrance | 0.15 |
| Hydrocarbon A-31 (Isobutane) | 25.00 |
| | 100.00 |

*Octylacrylamide/Acrylates/Butylamino ethyl Methacrylate

EXAMPLE 2

| Ingredients | Percent W/W |
| --- | --- |
| Ethanol Anhydrous | q.s. |
| 2-Amino-2 methyl-1 propanol | 0.32 |
| Stepanhold* | 2.00 |
| Water | 25.00 |
| Fragrance | 0.15 |
| Hydrocarbon A-31 (Isobutane) | 25.00 |
| | 100.00 |

*PVP/Ethyl Methacrylate/Methacrylic Acid

EXAMPLE 3

| Ingredients | Percent W/W |
| --- | --- |
| Ethanol Anhydrous | q.s. |
| 2-Amino-2 methyl-1 propanol | 0.30 |
| Methyl Methacrylate/Methacrylic Acid (80:20) | 1.50 |
| Water | 30.00 |
| Fragrance | 0.15 |
| Hydrocarbon A-31 (Isobutane) | 25.00 |
| | 100.00 |

In all the examples shown above, the amount of water used is critical. Below 2% water the flammability is not appreciably decreased and above 30%, the product is dispensed as a foam which is not desirable. Preferred results are obtained by the addition of 25% water.

We claim:
1. A hair spray composition comprising:
 (a) about 65 to 80 percent by weight of a liquid concentrate phase and,
 (b) about 20 to 35 percent by weight of a propellant phase consisting of a hydrocarbon;
the propellant phase selected from the group consisting of propane, n-butane, isobutane, or mixture thereof, said liquid concentrate phase based on the total weight of (a) and (b), from about 1 to 5 percent by weight of a water soluble film forming polymeric material selected from a group consisting of an acrylic resin, a methacrylic resin and mixtures thereof, from 2 to 30 percent by weight—water; from 0.4 to 2 percent by weight—of an organic base neutralizer for said polymeric material and sufficient ethanol or isopropanol, or mixtures thereof, to total 100 percent.

2. A composition according to claim 1 wherein said polymeric material is a copolymer of methyl methacrylate-methacrylic acid copolymer or a terpolymer of Octylacrylamide/Acrylates/Butylaminoethyl Methacrylate in which the acid groups are neutralized from 50 to 100 percent with an organic base.

3. A composition according to claim 2 wherein said organic base is selected from the group consisting of ammonia, dimethylamine, diethylamine, triethylamine, triisopropanolamine and 2-methyl-2-amino-1-propanol.

4. A composition according to claim 3 wherein said organic base is 2-methyl-2-amino-1-propanol.

5. A composition according to claim 1 wherein said liquid concentrate phase contains 25% water.

* * * * *